(12) United States Patent
Towns et al.

(10) Patent No.: US 9,228,817 B2
(45) Date of Patent: Jan. 5, 2016

(54) APPARATUS FOR MEASURING AN ARTICLE

(75) Inventors: Chris Towns, Taunton (GB); Peter Rickett, Englefield Green (GB); Dan Innes, London (GB); Yann Kinally, Middlesex (GB)

(73) Assignee: C & J CLARK INTERNATIONAL LIMITED, Street, Somerset (GB)

( * ) Notice: Subject to any disclaimer, the term of this patent is extended or adjusted under 35 U.S.C. 154(b) by 179 days.

(21) Appl. No.: 14/232,541

(22) PCT Filed: Jul. 9, 2012

(86) PCT No.: PCT/GB2012/051615
§ 371 (c)(1),
(2), (4) Date: Feb. 24, 2014

(87) PCT Pub. No.: WO2013/007997
PCT Pub. Date: Jan. 17, 2013

(65) Prior Publication Data
US 2014/0196301 A1    Jul. 17, 2014

(30) Foreign Application Priority Data
Jul. 13, 2011    (GB) .................................. 1111997.1

(51) Int. Cl.
| G01G 5/02 | (2006.01) |
| G01B 5/02 | (2006.01) |
| A43D 1/02 | (2006.01) |
| G01B 3/10 | (2006.01) |
| A43D 1/08 | (2006.01) |
| A61B 5/107 | (2006.01) |

(52) U.S. Cl.
CPC .. *G01B 5/02* (2013.01); *A43D 1/02* (2013.01); *A43D 1/08* (2013.01); *G01B 3/1084* (2013.01); *G01B 5/025* (2013.01); *A61B 5/1074* (2013.01)

(58) Field of Classification Search
CPC ..... G01B 5/02; G01B 5/0035; G01B 2210/58
USPC ................................... 33/755–771
See application file for complete search history.

(56) References Cited

U.S. PATENT DOCUMENTS

| 263,971 | A | | 9/1882 | Schaefer | |
| RE14,409 | E | * | 12/1917 | Saxton | ............................ 33/769 |
| 2,146,799 | A | * | 2/1939 | Davis, Jr. | ........................ 33/2 R |
| 2,636,281 | A | * | 4/1953 | Unger | .......................... 33/514.2 |
| 2,683,933 | A | | 7/1954 | McFarland | |

(Continued)

FOREIGN PATENT DOCUMENTS

| GB | 2492805 A | * | 1/2013 |
| NL | 1011049 C2 | | 7/2000 |
| SU | 1188510 A1 | | 10/1985 |

OTHER PUBLICATIONS

International Search Report Application No. PCT/GB2012/051615 Completed: Sep. 12, 2012; Mailing Date: Sep. 20, 2012 3 pages.

*Primary Examiner* — Yaritza Guadalupe-McCall
(74) *Attorney, Agent, or Firm* — Squirre Patton Boggs (US) LLP

(57) ABSTRACT

There is provided a measuring device having a pair of pivoted arms, the ends of which remote from the pivot having an associated tape. The tape is fixed to one arm and extends internally through the other arm to be wound on to a biased reel located in a housing part, the reel taking up any slack in the tape.

20 Claims, 6 Drawing Sheets

(56) References Cited

U.S. PATENT DOCUMENTS

| | | | |
|---|---|---|---|
| 4,265,021 A * | 5/1981 | Campbell | 33/783 |
| 4,453,680 A * | 6/1984 | Miller | 33/769 |
| 4,688,653 A * | 8/1987 | Ruble | 33/759 |
| 5,062,215 A * | 11/1991 | Schlitt | 33/755 |
| 5,174,030 A | 12/1992 | Clot et al. | |
| 5,184,407 A | 2/1993 | Watrous | |
| 5,193,287 A * | 3/1993 | Coulter et al. | 33/555.4 |
| 5,367,785 A * | 11/1994 | Benarroch | 33/767 |
| 5,371,949 A * | 12/1994 | Delaurier | 33/1 G |
| 5,430,951 A * | 7/1995 | Jacky | 33/760 |
| 5,613,302 A * | 3/1997 | Berman et al. | 33/514.2 |
| 6,209,213 B1 | 4/2001 | Moe | |
| 6,253,459 B1 * | 7/2001 | Barnhill | 33/514.1 |
| 6,598,310 B1 * | 7/2003 | Odachowski | 33/755 |
| 6,640,460 B1 * | 11/2003 | Nabarro et al. | 33/759 |
| 6,817,110 B2 * | 11/2004 | Bohnengel | 33/555.4 |
| 6,978,553 B2 * | 12/2005 | Doublet | 33/756 |
| 7,047,659 B2 * | 5/2006 | Holland | 33/760 |
| 7,146,743 B2 * | 12/2006 | Oura | 33/756 |
| 7,552,538 B1 * | 6/2009 | Bushman et al. | 33/195 |
| 8,146,261 B1 * | 4/2012 | Perry | 33/511 |
| 2002/0184779 A1 * | 12/2002 | Bohnengel | 33/555.4 |
| 2014/0196301 A1 * | 7/2014 | Towns et al. | 33/769 |

* cited by examiner

APPARATUS FOR MEASURING AN ARTICLE

FIELD OF THE INVENTION

The present invention relates to apparatus for measuring an article, particularly but not exclusively for measuring the girth or partial girth of an article. The apparatus finds particular use in measuring the girth of a foot for correct fitting of footwear.

SUMMARY OF THE INVENTION

According to the present invention there is provided apparatus for measuring an article, the apparatus comprising: a pair of arms which are movable with respect to each other about a pivot, each arm having an end remote from the pivot; a flexible, elongate measuring element associated with the ends of the arms such that the measuring element has one extremity fixed with respect to the end of one arm and is able to move relative to a guide provided at the end of the other arm, the other extremity of the measuring element being secured to a reel which is biased to take up any slack in the measuring element.

Preferably, the other ends of the arms are each attached to respective cooperating housing parts which are rotatable relative to each other and which incorporate the pivot, the reel being coaxial with the pivot and free to rotate relative to both housing parts.

In preferred arrangements said other arm has an internal passage through which the measuring element can move, the passage opening at the free end of said other arm remote from the pivot to constitute said guide and leading at the pivot end of the arm to said reel.

Conveniently, the two arms are generally L-shaped and face in opposite directions, the two ends remote from the pivot abutting each other and also the end of each arm remote from the pivot tapers inwardly.

Normally the measuring element is in the form of a tape.

It is a preferred feature that biasing means urges the ends of the two arms towards each other and usually the biasing means for the two arms also biases the reel. The biasing action may utilize a clockspring.

A useful feature is that the reel includes a holding mechanism for locking the measuring element when a measurement is to be taken.

In preferred embodiments the reel incorporates a digital measuring device for measuring the length of measuring element paid out relative to said guide when the ends of the two arms are moved apart and said article is being measured, the digital measuring device having a display for indicating the length of measuring element paid out.

In further preferred arrangements the digital measuring device also measures the angular displacement of the arms in order to calculate the linear distance between the free ends of the arms, this linear distance being capable of being shown on the display.

BRIEF DESCRIPTION OF THE DRAWINGS

Embodiments of the invention will now be described in more detail. The description makes reference to the accompanying drawings in which.

DETAILED DESCRIPTION OF THE INVENTION

Figure 1:
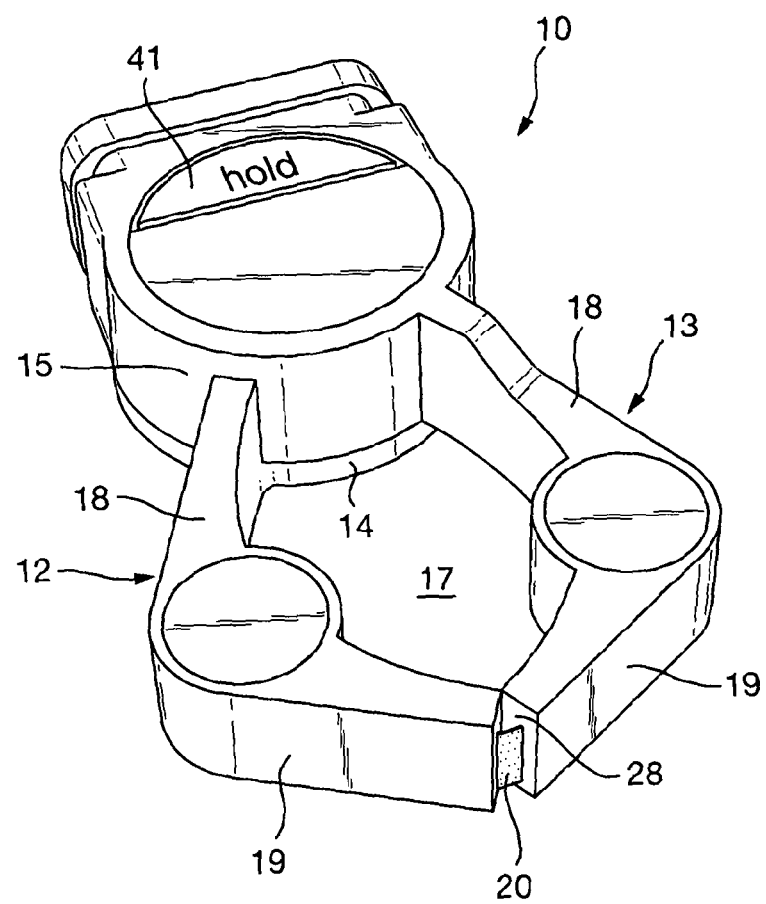
FIG. 1 is a perspective view of a measuring device according to the present invention.

In the figures there is shown a measuring device 10 which is particularly useful for measuring the girth of a foot 11 although the device 10 can be used for measuring the girth or partial girth of other objects and can also be used to measure linear distances. When measuring girth for footwear, the person usually stands on the floor and the girth measurement is taken from one side of the foot where it meets the floor and over the top of the foot to the other side of the floor where it meets the floor. This is indicated more clearly in FIG. 5.

The device 10 has a pair of arms 12, 13. One of the arms 12 is attached to a rear housing part 14 and the other arm 13 is attached to a forward housing part 15. The two housing parts 14, 15 are connected together so as to be rotatable relative to each other about a central pivot 16. Other housing constructions are possible provided the two arms are able to pivot relative to each other.

Figure 5A:
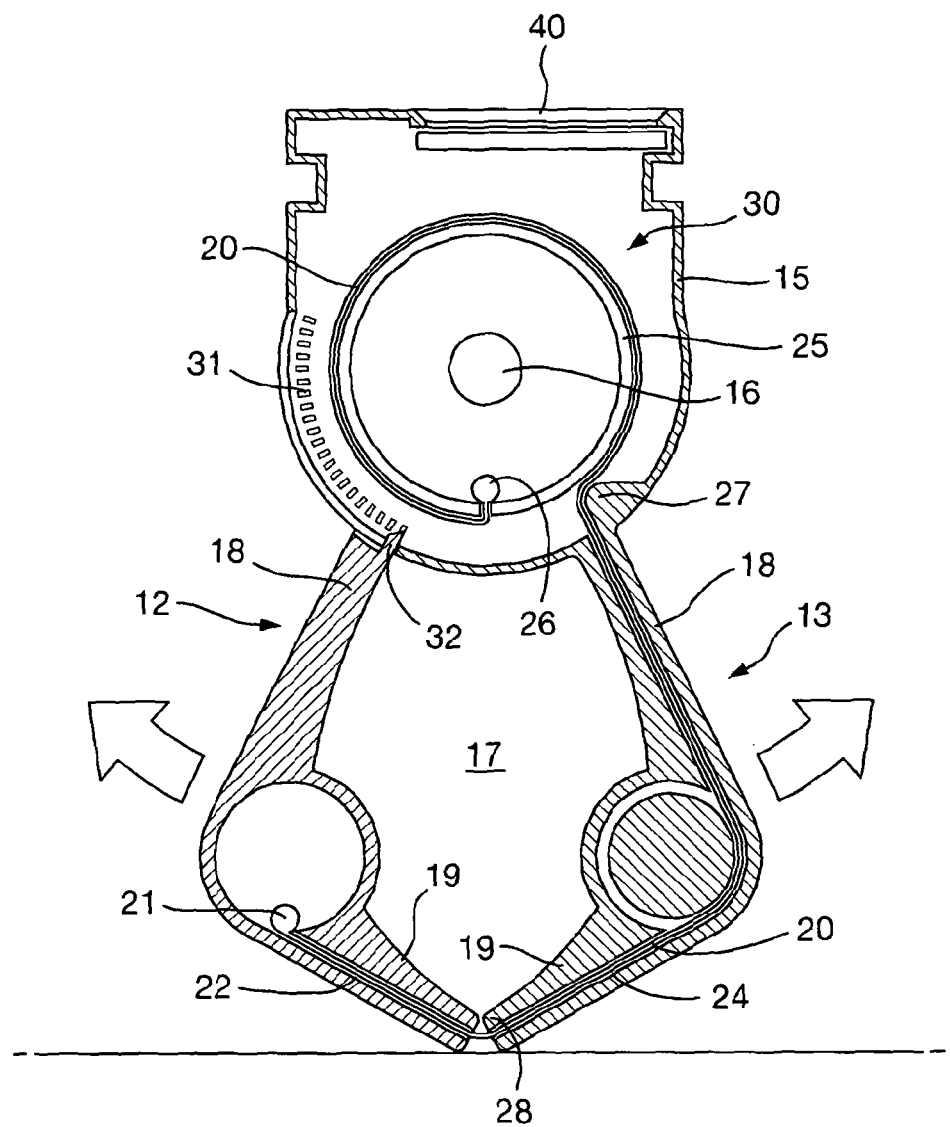
FIG. 5*a* is a vertical section through the measuring device of FIG. 1 not in use.

In the illustrated arrangement the two arms 12, 13 are generally L-shaped but oppositely disposed so as to leave a space 17 between the two arms, which space 17 can be beneficial when measuring the girth of certain articles. The 'upright' part 18 of each L-shaped arm 12, 13 is generally aligned with the pivot 16 such that the 'lower' part 19 of each L-shaped arm 12, 13 is somewhat angled relative to the floor. Ideally the two arms 12, 13 are biased towards each other by suitable biasing means such as a clockspring (not shown) so that the free ends of the lower parts 19 abut as illustrated in FIGS. 1 and 5*a* when in an 'at rest' position. Other arm shapes would of course be possible depending somewhat on the end use of the device 10.

The measuring device 10 includes a flexible, elongate measuring element 20 which is in the form of a length of tape in the illustrated embodiment but could take another form such as a cord. One extremity 21 of the tape 20 is fixed with respect to said one arm 12 and in the illustrated embodiment the tape 20 extends along an internal passage 22 and the extremity 21 is held internally in a hollow section 23 of the arm 12 where the two parts 18, 19 of the L-shape meet.

The tape 20 also passes through another internal passage 24 in the other arm 13 and extends the full length of the arm 13 to the housing 14, 15 where it is attached to a reel 25 at location 26. The reel 25 is rotatably mounted on the pivot 16 and is biased in an anti-clockwise direction by a biasing means such as a return spring (not shown) for example so as to take up any slack in the tape 20. The forward housing part 15 also incorporates an internal guide surface 27 to facilitate a smooth transition of the tape 12 between the arm 13 and the reel 25.

The free ends of the two arms 12, 13 are tapered so as to be generally pointed and the extreme free end 28 of the other arm 13 constitutes a simple guide for movement of the tape 20 during use. More complicated guides could be devised if desired. The pointed form of the free ends of the two arms 12, 13 enables the arms to abut closely when at rest and to enable access to tight spaces when in use, such as when positioned below a foot which tends to overhang the contact points with the floor or other supporting surface. The extreme free ends of the arms 12, 13 constitute the measurement reference points.

Figure 2:
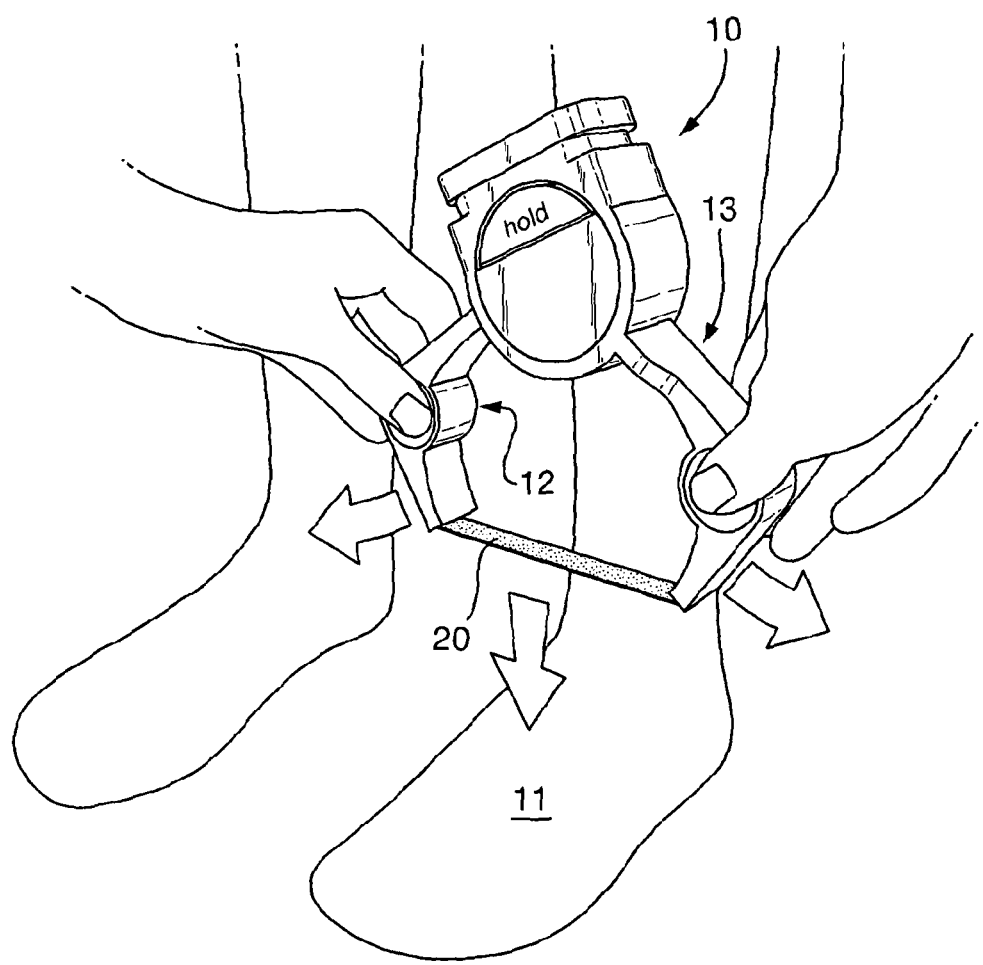
FIG. 2 is a perspective view of the measuring device of FIG. 1 about to be used to measure the girth of a foot.
Figure 3:
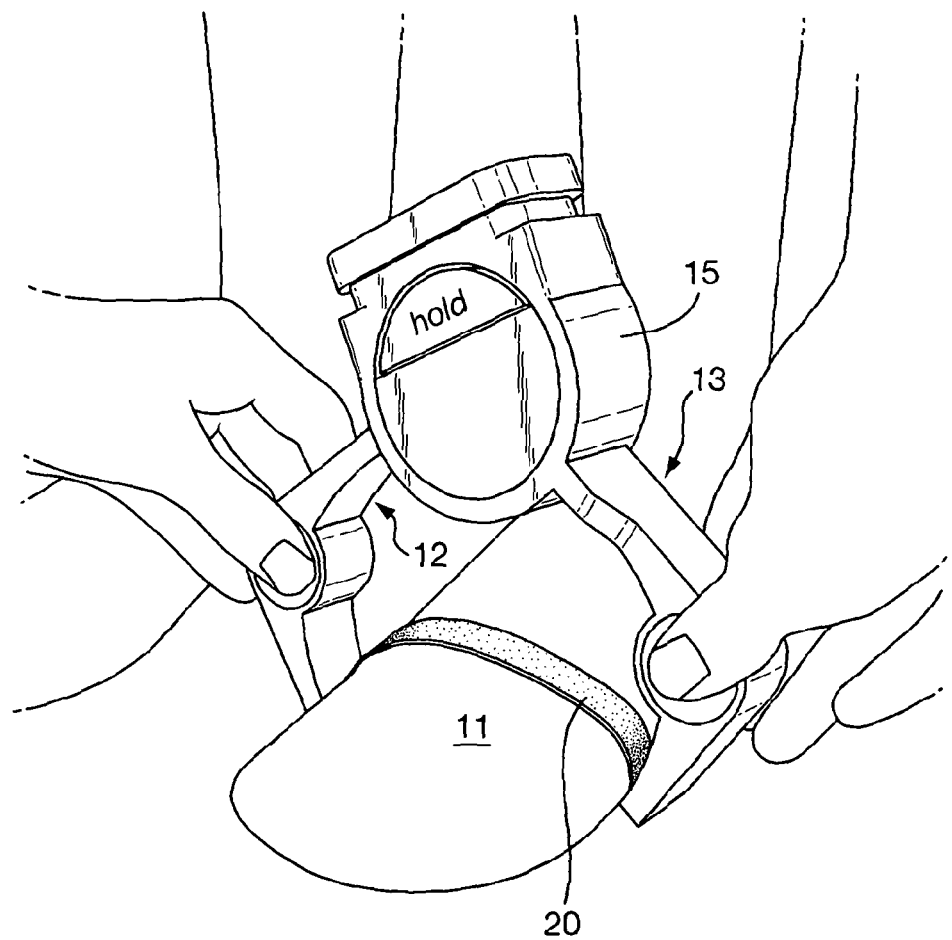
FIG. 3 is a perspective view of the measuring device of FIG. 1 in position relative to the foot.
Figure 4:
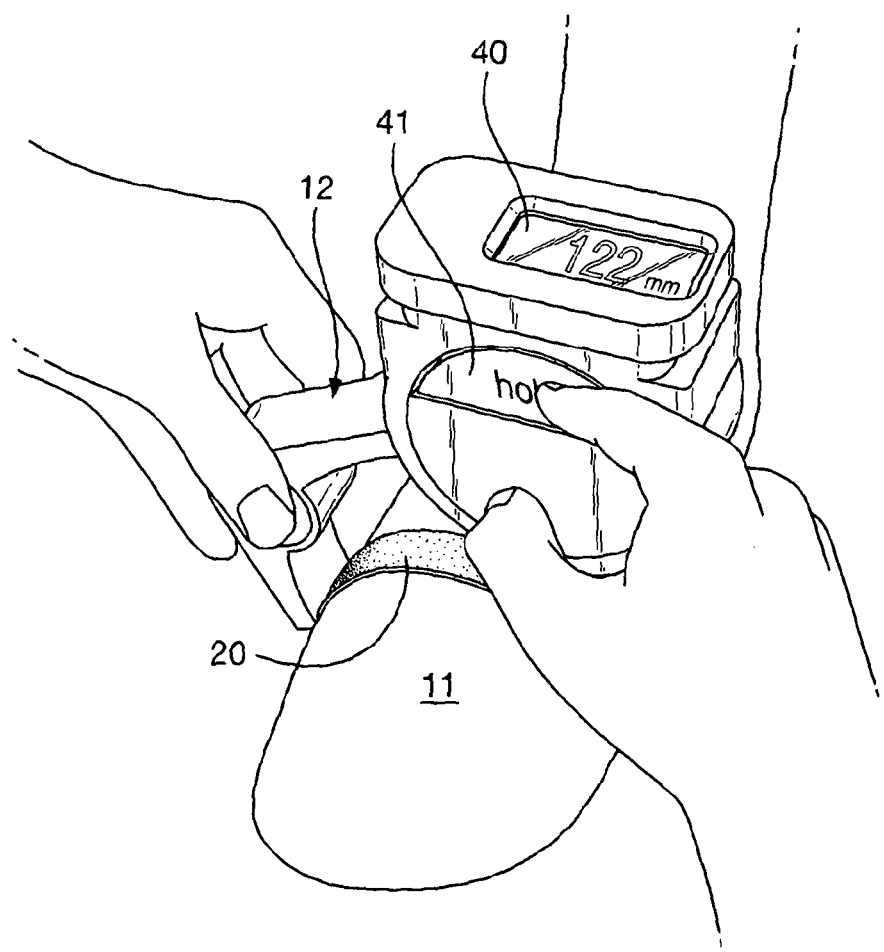
FIG. 4 is a perspective view of the measuring device of FIG. 1 showing a measurement being taken.

The housing parts 14, 15 also accommodate a digital measuring arrangement 30. Digital measuring arrangements are known but have been adapted for the present use. As an example, one form of digital measuring device 30 provides a digital scale 31 associated with the forward housing part 15 and an actuator 32 associated with said one arm 12. When the two arms 12, 13 are rotated relative to each other, i.e. opened up as shown in FIG. 2, tape 20 is paid out as the reel 25 rotates clockwise relative to the forward housing part 15 against the biasing force and the tape 20 extends in a generally straight line between the free ends of the two arms 12, 13. Movement of the two arms 12, 13 relative to each other results in the actuator 32 moving around the digital scale 31. The linear distance between the free ends of the arms is a function of the movement of the actuator 32 along the digital scale 31 which is calibrated to give a length output. The angular separation X of the two arms relative to the closed position, combined with the known distance from the arm ends to the pivot axis enables this linear distance to be calculated using software.

Figure 5B:
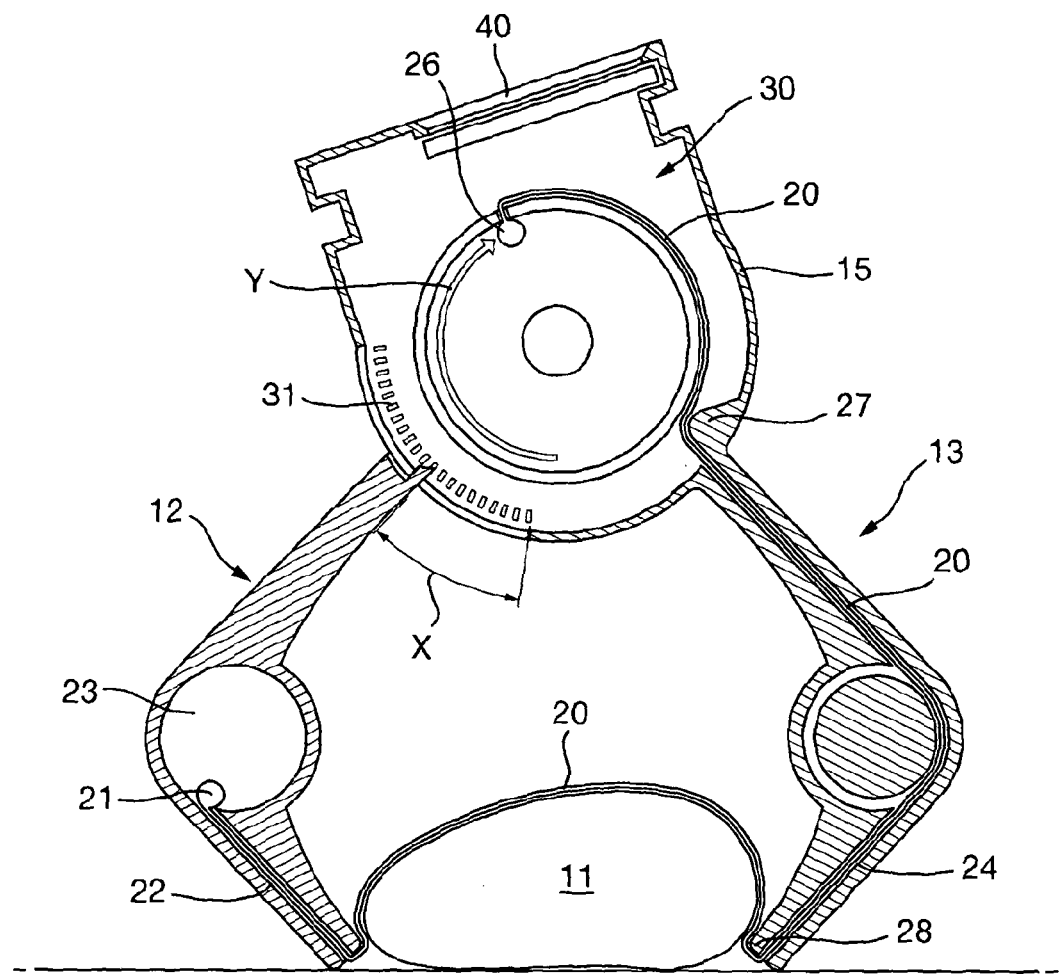
FIG. 5*b* is a vertical section through the measuring device of FIG. 1 in use measuring a foot.

When the device is placed around a three dimensional object, such as a foot 11 in FIG. 5*b*, more tape 20 is paid out by the drum 25 so as to follow the contour of the foot. The free ends of the two arms 12, 13 which constitute the measurement reference points, are moved into their correct positions below the lateral overhangs of the foot 11 as shown in FIG. 5. The length of tape 20 between the two free ends of the arms 12, 13 is the "over the foot" girth measurement that is required and the linear distance between the free ends of the arms is known as the tread width.

The clockwise rotation of the reel 25 against the biasing action causes any unwanted slack in the tape 20 to be taken up so as to ensure correct measurement. The rotation Y of the reel 25 gives a measure of the total amount of tape 20 which has been dispensed, this amount being a measure of the distance over the top of the foot from floor to floor. Again calibration of the digital measuring arrangement 30 together with the known reel dimensions is such that an output is provided for the total length of tape 20 between the two measurement reference points.

In addition, it is preferable for the software of the digital measuring arrangement 30 to provide a total girth or circumference measurement by means of an addition of the tread width, i.e. the linear distance between the ends of the arm (measured by the relative angular displacement of the arms) and the "over the foot" measurement (measured by the amount of tape 20 dispensed by the reel). This total girth measurement in a "weight on" condition, coupled with the other measurements gives a true indication of foot width/girth dimensions for improved shoe fitting.

The digital measuring arrangement 30 can, in preferred arrangements, take the following form although other methods are possible within the scope of the invention. A radially extending set of resistive electro contacts are located on the side of the tape reel 25 and these contacts bridge a circular array of contacts located on a static PCB (Printed Circuit Board). When the arms 12, 13 are closed, the contacts provide a zero reading but as the arms are opened and tape 20 is dispensed, the relative movement of the reel contacts and the PCB contacts relays a value of the length of tape dispensed as the reel rotates.

The device 10 also incorporates a display screen 40 which displays the total length of tape 20 paid out and also a 'hold' button 41. The hold button 41 is pressed when the arms 12, 13 are in their correct measuring position. The button 41 effectively locks movement of the reel 25 relative to the housing 14, 15 so that the total length displayed on the screen 40 can be set when the arms are correctly positioned. This can be beneficial if the foot belongs to someone prone to movement, such as a child. The locking action of the reel 25 can be by simple means such as the button engaging the reel to prevent rotation.

The precise design of the measuring device is open to modification whilst remaining within the scope of the claims. In its simplest form, the tape 20 could have measurements printed thereon and the digital measuring arrangement 30 could be omitted.

The invention claimed is:

1. Apparatus for measuring an article, the apparatus comprising: a pair of arms which are movable with respect to each other about a pivot, each arm having an end remote from the pivot; a flexible, elongate measuring element associated with the ends of the arms such that the measuring element has one extremity fixed with respect to the end of one arm and is able to move relative to a guide provided at the end of the other arm, the other extremity of the measuring element being secured to a reel which is biased to take up any slack in the measuring element.

2. Apparatus as claimed in claim 1 wherein the other ends of the arms are each attached to respective cooperating housing parts which are rotatable relative to each other and which incorporate the pivot, the reel being coaxial with the pivot and free to rotate relative to both housing parts.

3. Apparatus as claimed in claim 2 wherein said other arm has an internal passage through which the measuring element can move, the passage opening at the free end of said other arm remote from the pivot to constitute said guide and leading at the pivot end of the arm to said reel.

4. Apparatus as claimed in claim 3 wherein the two arms are generally L-shaped and face in opposite directions, the two ends remote from the pivot abutting each other.

5. Apparatus as claimed in claim 4 wherein the end of each arm remote from the pivot tapers inwardly.

6. Apparatus as claimed in claim 1 wherein the measuring element is in the form of a tape.

7. Apparatus as claimed in claim 1 wherein biasing means urges the ends of the two arms towards each other.

8. Apparatus as claimed in claim 7 wherein the biasing means for the two arms also biases the reel.

9. Apparatus as claimed in claim 7 wherein the or each biasing means comprises a clockspring.

10. Apparatus as claimed in claim 1 wherein the reel includes a holding mechanism for locking the measuring element when a measurement is to be taken.

11. Apparatus as claimed in claim 1 wherein the reel incorporates a digital measuring device for measuring the length of measuring element paid out relative to said guide when the ends of the two arms are moved apart and said article is being measured, the digital measuring device having a display for indicating the length of measuring element paid out.

12. Apparatus as claimed in claim 11 wherein the digital measuring device also measures the angular displacement of the arms in order to calculate the linear distance between the free ends of the arms, this linear distance being capable of being shown on the display.

13. Apparatus as claimed in claim 12 wherein the digital measuring device is capable of adding the linear distance to the length of measuring element paid out to provide a total girth measurement and to show this on the display.

14. A measuring apparatus comprising:
a housing;
two arms extending from the housing, each arm having an end, at least one arm being pivotable relative to the other arm;
a spiral clockspring which biases the two arms towards each other;
a flexible measuring element having an extremity affixed to one arm and extending from the end of the one arm, and being slidable within the end of the other arm, and having another extremity secured to a spring-biased reel.

15. The measuring apparatus of claim 14, wherein the two arms each have a first part extending from the housing and a second part extending at an angle from the first part, with the second parts of the two arms extending towards each other such that the ends of the arms contact each other.

16. The measuring apparatus of claim 15 wherein the measuring element is a tape or a cord.

17. The measuring apparatus of claim 16 where the spiral clockspring provides the spring bias for the reel.

18. The measuring apparatus of claim 16 further comprising a lock mechanism for locking the housing to prevent pivoting of one arm relative to the other arm.

19. The measuring apparatus of claim 16 further comprising a digital display for displaying measurements made using the measuring apparatus.

20. The measuring apparatus of claim 19 further comprising a digital measuring device which detects angular displacement of the arms when an arm is pivoted relative to the other arm and calculates the linear distance between the free ends of the arms.

* * * * *